US007060477B2

(12) United States Patent
Arand et al.

(10) Patent No.: US 7,060,477 B2
(45) Date of Patent: Jun. 13, 2006

(54) **EPOXIDE HYDROLASES OF *ASPERGILLUS* ORIGIN**

(75) Inventors: Michael Arand, Mainz-Kastheim (DE); Alain R. Archelas, Marseilles (FR); Jacques Baratti, La Ciotat (FR); Roland Furstoss, Marseilles (FR)

(73) Assignees: Centre National de la Recherche Scientifique (FR); Universite de la Mediterranee (FR)

( * ) Notice: Subject to any disclaimer, the term of this patent is extended or adjusted under 35 U.S.C. 154(b) by 0 days.

(21) Appl. No.: 10/009,030

(22) PCT Filed: May 5, 2000

(86) PCT No.: PCT/FR00/01217

§ 371 (c)(1), (2), (4) Date: Aug. 19, 2002

(87) PCT Pub. No.: WO00/68394

PCT Pub. Date: Nov. 16, 2000

(65) Prior Publication Data

US 2003/0143710 A1    Jul. 31, 2003

(30) Foreign Application Priority Data

May 5, 1999    (FR) .................................... 99 05711

(51) Int. Cl.
*C12N 9/14*   (2006.01)
*C12N 15/55*  (2006.01)
*C12P 17/02*  (2006.01)
*C12P 7/18*   (2006.01)

(52) U.S. Cl. ...................... 435/195; 435/123; 435/158; 435/252.3; 435/326.1; 536/23.2

(58) Field of Classification Search ................ 435/195, 435/252.3, 320.1, 123, 158; 536/23.2
See application file for complete search history.

(56) References Cited

U.S. PATENT DOCUMENTS 5,849,568 A  * 12/1998 Chartrain et al. ........... 435/280

OTHER PUBLICATIONS

Morisseau, C., et al. (1997) Enz. Microb. Tech. 20, 446-452.*
Morisseau, C., er all. (1999) Eur. J. Biochem. 263, 386-395.*
Archelas et al, "Epoxide . . . Chemicals", Trends in Biotechnology, GB, Elsevier Publications, Cambridge, vol. 16, No. 3, Mar. 1, 1998 pp. 108-116.
Moassou et al, "Microgiological Transformations 40. Use . . . Epoxides", Tetrahedron, NL, Elsevier Science Publishers, Amsterdam, vol. 54, No. 8, Feb. 19, 1998 pp. 1563-1572.
Cleij et al, "Microbiological . . . Enhancement", Tetrahedron: Asymmetry, NL, Elsevier Science Publishers, Amsterdam, vol. 09, No. 11, Jun. 5, 1998, pp. 1839-1842.
Nellaiah et al, "Enantioselective . . . *Aspergillus niger*", Biotechnology and Bioengineering, vol. 49, 1996, pp. 70-77, XP002130510.
Kupfer et al, "An . . . Database", Feb. 2, 1998, XP002130511.
Arand et al, "Cloning . . . Hydrolase", Biochemical Journal, vol. 344, Nov. 15, 1999, pp. 273-280, XP000938551.

* cited by examiner

*Primary Examiner*—Charles L. Patterson, Jr.
(74) *Attorney, Agent, or Firm*—Charles A. Muserlian

(57) ABSTRACT

The invention concerns proteins of fungal origin having an epoxide hydrolase activity, such as those obtained in essentially pure form by extraction from fungi cells, or by culturing in host cells transformed by a nucleotide sequence coding for said fungal proteins. The invention also concerns the uses thereof, in particular for implementing methods for preparing enantiopure epoxides and/or diols.

8 Claims, No Drawings

SEQUENCE LISTING

```
<160> NUMBER OF SEQ ID NOS: 8

<210> SEQ ID NO 1
<211> LENGTH: 1197
<212> TYPE: DNA
<213> ORGANISM: Aspergillus niger
<220> FEATURE:
```

-continued

<221> NAME/KEY: CDS
<222> LOCATION: (1)..(1194)

<400> SEQUENCE: 1

| | | | | | | | | | | | | | | | | |
|---|---|---|---|---|---|---|---|---|---|---|---|---|---|---|---|---|
| atg | tcc | gct | ccg | ttc | gcc | aag | ttt | ccc | tcg | tcg | gcg | agc | att | tcg | cct | 48 |
| Met | Ser | Ala | Pro | Phe | Ala | Lys | Phe | Pro | Ser | Ser | Ala | Ser | Ile | Ser | Pro | |
| 1 | | | | 5 | | | | | 10 | | | | | 15 | | |
| aat | cct | ttc | acg | gtc | tct | atc | ccg | gat | gaa | cag | ttg | gat | gac | ttg | aaa | 96 |
| Asn | Pro | Phe | Thr | Val | Ser | Ile | Pro | Asp | Glu | Gln | Leu | Asp | Asp | Leu | Lys | |
| | | | 20 | | | | | 25 | | | | | 30 | | | |
| acc | ctc | gtc | cga | ctg | tcc | aag | att | gct | cct | ccc | acc | tat | gag | agc | ctg | 144 |
| Thr | Leu | Val | Arg | Leu | Ser | Lys | Ile | Ala | Pro | Pro | Thr | Tyr | Glu | Ser | Leu | |
| | | 35 | | | | | 40 | | | | | 45 | | | | |
| caa | gcg | gat | ggc | cgg | ttt | ggc | atc | act | tct | gaa | tgg | ctg | aca | act | atg | 192 |
| Gln | Ala | Asp | Gly | Arg | Phe | Gly | Ile | Thr | Ser | Glu | Trp | Leu | Thr | Thr | Met | |
| | 50 | | | | | 55 | | | | | 60 | | | | | |
| cgg | gag | aaa | tgg | ctc | tcg | gag | ttt | gac | tgg | cga | cca | ttt | gaa | gct | cga | 240 |
| Arg | Glu | Lys | Trp | Leu | Ser | Glu | Phe | Asp | Trp | Arg | Pro | Phe | Glu | Ala | Arg | |
| 65 | | | | | 70 | | | | | 75 | | | | | 80 | |
| ctg | aac | tct | ttc | cct | cag | ttt | act | aca | gag | atc | gag | ggt | ctc | acg | att | 288 |
| Leu | Asn | Ser | Phe | Pro | Gln | Phe | Thr | Thr | Glu | Ile | Glu | Gly | Leu | Thr | Ile | |
| | | | | 85 | | | | | 90 | | | | | 95 | | |
| cac | ttt | gct | gct | ctc | ttc | tcc | gag | agg | gag | gat | gct | gtg | cct | atc | gca | 336 |
| His | Phe | Ala | Ala | Leu | Phe | Ser | Glu | Arg | Glu | Asp | Ala | Val | Pro | Ile | Ala | |
| | | | | 100 | | | | | 105 | | | | | 110 | | |
| ttg | ctc | cat | ggt | tgg | ccc | ggc | agc | ttc | gtt | gag | ttc | tac | cca | atc | ctg | 384 |
| Leu | Leu | His | Gly | Trp | Pro | Gly | Ser | Phe | Val | Glu | Phe | Tyr | Pro | Ile | Leu | |
| | | | 115 | | | | | 120 | | | | | 125 | | | |
| cag | cta | ttc | cgg | gag | gag | tac | acc | cct | gag | act | ctg | cca | ttc | cat | ctg | 432 |
| Gln | Leu | Phe | Arg | Glu | Glu | Tyr | Thr | Pro | Glu | Thr | Leu | Pro | Phe | His | Leu | |
| | 130 | | | | | 135 | | | | | 140 | | | | | |
| gtt | gtt | ccg | tcc | ctt | cct | ggg | tat | act | ttt | tca | tct | ggt | ccc | ccg | ctg | 480 |
| Val | Val | Pro | Ser | Leu | Pro | Gly | Tyr | Thr | Phe | Ser | Ser | Gly | Pro | Pro | Leu | |
| 145 | | | | | 150 | | | | | 155 | | | | | 160 | |
| gac | aag | gac | ttc | ggc | ttg | atg | gac | aac | gcc | cgg | gtc | gta | gac | cag | ttg | 528 |
| Asp | Lys | Asp | Phe | Gly | Leu | Met | Asp | Asn | Ala | Arg | Val | Val | Asp | Gln | Leu | |
| | | | | 165 | | | | | 170 | | | | | 175 | | |
| atg | aag | gac | ctc | ggg | ttc | gga | agt | ggt | tat | att | att | cag | gga | ggt | gat | 576 |
| Met | Lys | Asp | Leu | Gly | Phe | Gly | Ser | Gly | Tyr | Ile | Ile | Gln | Gly | Gly | Asp | |
| | | | | 180 | | | | | 185 | | | | | 190 | | |
| att | ggt | agc | ttt | gtt | gga | cga | ctg | ttg | ggc | gtg | ggt | ttc | gac | gcc | tgc | 624 |
| Ile | Gly | Ser | Phe | Val | Gly | Arg | Leu | Leu | Gly | Val | Gly | Phe | Asp | Ala | Cys | |
| | | | 195 | | | | | 200 | | | | | 205 | | | |
| aaa | gcg | gtt | cat | ttg | aac | ctg | tgc | gca | atg | agg | gct | ccc | cct | gag | ggc | 672 |
| Lys | Ala | Val | His | Leu | Asn | Leu | Cys | Ala | Met | Arg | Ala | Pro | Pro | Glu | Gly | |
| | 210 | | | | | 215 | | | | | 220 | | | | | |
| ccg | tca | att | gag | agc | ttg | tcc | gca | gcg | gag | aag | gag | gga | atc | gcg | cga | 720 |
| Pro | Ser | Ile | Glu | Ser | Leu | Ser | Ala | Ala | Glu | Lys | Glu | Gly | Ile | Ala | Arg | |
| 225 | | | | | 230 | | | | | 235 | | | | | 240 | |
| atg | gag | aag | ttc | atg | acc | gat | ggc | tta | gct | tat | gcc | atg | gag | cac | agt | 768 |
| Met | Glu | Lys | Phe | Met | Thr | Asp | Gly | Leu | Ala | Tyr | Ala | Met | Glu | His | Ser | |
| | | | | 245 | | | | | 250 | | | | | 255 | | |
| act | cgg | ccc | agt | act | att | ggc | cac | gtg | ctg | tcc | agc | agt | ccg | atc | gca | 816 |
| Thr | Arg | Pro | Ser | Thr | Ile | Gly | His | Val | Leu | Ser | Ser | Ser | Pro | Ile | Ala | |
| | | | 260 | | | | | 265 | | | | | 270 | | | |
| tta | ctt | gca | tgg | att | ggt | gag | aaa | tat | ctc | caa | tgg | gtg | gat | aaa | ccc | 864 |
| Leu | Leu | Ala | Trp | Ile | Gly | Glu | Lys | Tyr | Leu | Gln | Trp | Val | Asp | Lys | Pro | |
| | 275 | | | | | 280 | | | | | 285 | | | | | |
| ctc | cct | tct | gag | acc | atc | ctc | gag | atg | gtg | agc | ctg | tat | tgg | ctg | acg | 912 |
| Leu | Pro | Ser | Glu | Thr | Ile | Leu | Glu | Met | Val | Ser | Leu | Tyr | Trp | Leu | Thr | |

```
                    290                 295                 300
gaa agt ttc ccg cgg gca att cat acc tac cgc gag act acc cca act      960
Glu Ser Phe Pro Arg Ala Ile His Thr Tyr Arg Glu Thr Thr Pro Thr
305                 310                 315                 320 gcc tcc gct ccc aat gga gcg aca atg ctt cag aag gaa tta tat att     1008
Ala Ser Ala Pro Asn Gly Ala Thr Met Leu Gln Lys Glu Leu Tyr Ile
                325                 330                 335 cac aag ccg ttt ggg ttc tcc ttc ttc ccc aag gac ctt tgt cct gtg     1056
His Lys Pro Phe Gly Phe Ser Phe Phe Pro Lys Asp Leu Cys Pro Val
    340                 345                 350 cct cgg agc tgg att gct aca acg gga aat cta gta ttc ttc cgg gat     1104
Pro Arg Ser Trp Ile Ala Thr Thr Gly Asn Leu Val Phe Phe Arg Asp
            355                 360                 365 cat gca gag gga gga cac ttt gcc gca ttg gag cgt cca cgc gag ctg     1152
His Ala Glu Gly Gly His Phe Ala Ala Leu Glu Arg Pro Arg Glu Leu
        370                 375                 380 aag acc gac ctg aca gca ttt gtc gag cag gtg tgg cag aag tag         1197
Lys Thr Asp Leu Thr Ala Phe Val Glu Gln Val Trp Gln Lys
385                 390                 395
```

<210> SEQ ID NO 2
<211> LENGTH: 398
<212> TYPE: PRT
<213> ORGANISM: Aspergillus niger

<400> SEQUENCE: 2

```
Met Ser Ala Pro Phe Ala Lys Phe Pro Ser Ala Ser Ile Ser Pro
1               5                   10                  15

Asn Pro Phe Thr Val Ser Ile Pro Asp Glu Gln Leu Asp Leu Lys
            20                  25                  30

Thr Leu Val Arg Leu Ser Lys Ile Ala Pro Pro Thr Tyr Glu Ser Leu
        35                  40                  45

Gln Ala Asp Gly Arg Phe Gly Ile Thr Ser Glu Trp Leu Thr Thr Met
    50                  55                  60

Arg Glu Lys Trp Leu Ser Glu Phe Asp Trp Arg Pro Phe Glu Ala Arg
65                  70                  75                  80

Leu Asn Ser Phe Pro Gln Phe Thr Thr Glu Ile Glu Gly Leu Thr Ile
                85                  90                  95

His Phe Ala Ala Leu Phe Ser Glu Arg Glu Asp Ala Val Pro Ile Ala
            100                 105                 110

Leu Leu His Gly Trp Pro Gly Ser Phe Val Glu Phe Tyr Pro Ile Leu
        115                 120                 125

Gln Leu Phe Arg Glu Glu Tyr Thr Pro Glu Thr Leu Pro Phe His Leu
    130                 135                 140

Val Val Pro Ser Leu Pro Gly Tyr Thr Phe Ser Ser Gly Pro Pro Leu
145                 150                 155                 160

Asp Lys Asp Phe Gly Leu Met Asp Asn Ala Arg Val Val Asp Gln Leu
                165                 170                 175

Met Lys Asp Leu Gly Phe Gly Ser Gly Tyr Ile Ile Gln Gly Gly Asp
            180                 185                 190

Ile Gly Ser Phe Val Gly Arg Leu Leu Gly Val Gly Phe Asp Ala Cys
        195                 200                 205

Lys Ala Val His Leu Asn Leu Cys Ala Met Arg Ala Pro Pro Glu Gly
    210                 215                 220

Pro Ser Ile Glu Ser Leu Ser Ala Ala Glu Lys Glu Gly Ile Ala Arg
225                 230                 235                 240
```

```
Met Glu Lys Phe Met Thr Asp Gly Leu Ala Tyr Ala Met Glu His Ser
                245                 250                 255

Thr Arg Pro Ser Thr Ile Gly His Val Leu Ser Ser Pro Ile Ala
        260                 265                 270

Leu Leu Ala Trp Ile Gly Glu Lys Tyr Leu Gln Trp Val Asp Lys Pro
            275                 280                 285

Leu Pro Ser Glu Thr Ile Leu Glu Met Val Ser Leu Tyr Trp Leu Thr
        290                 295                 300

Glu Ser Phe Pro Arg Ala Ile His Thr Tyr Arg Glu Thr Thr Pro Thr
305                 310                 315                 320

Ala Ser Ala Pro Asn Gly Ala Thr Met Leu Gln Lys Glu Leu Tyr Ile
                325                 330                 335

His Lys Pro Phe Gly Phe Ser Phe Phe Pro Lys Asp Leu Cys Pro Val
            340                 345                 350

Pro Arg Ser Trp Ile Ala Thr Thr Gly Asn Leu Val Phe Phe Arg Asp
        355                 360                 365

His Ala Glu Gly Gly His Phe Ala Ala Leu Glu Arg Pro Arg Glu Leu
    370                 375                 380

Lys Thr Asp Leu Thr Ala Phe Val Glu Gln Val Trp Gln Lys
385                 390                 395

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 3
atgcgatcgg actgctggac a                                          21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
cgcgggcaat ccacacctac                                            20

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 5
cggaattcca tggtcactgg aggagcaata attag                           35

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 6
ttgaattccc tacttctgcc acac                                       24
```

-continued

```
<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 7
gctgaattca catgtccgct ccgttcgcca ag                               32

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ccatgggaat tctcgagatc taagcttatg catcagctgc atgg                  44
```

EPOXIDE HYDROLASES OF *ASPERGILLUS* ORIGIN

This application is a 371 of PCT/FR00/01217 filed May 5, 2000.

The present invention relates to proteins of fungal origin or proteins derived from the latter, possessing epoxide hydrolase activity, as well as their uses, notably for the preparation of enantiomerically pure (or enantiopure) molecules, such as epoxides and/or vicinal diols of high enantiomeric purity.

The epoxides or the vicinal diols are important compounds in organic synthesis. If they have a chiral structure, they can be used either in the racemic form, or in the optically enriched or even enantiomerically pure form. In the first case they constitute base products for the chemical industry (polymerizable monomers or components of industrial products such as glycol, propyleneglycol etc.). In the second case they can be used as chiral synthons for the production of various optically pure products, for example biologically active molecules marketed by the pharmaceutical or plant-protection industry, or materials with specific optical properties (e.g. liquid crystals).

This is why various strategies of chemical synthesis have been elaborated for carrying out their production. With regard to the production of diols, these strategies often involve the hydrolysis of an epoxide in a more or less concentrated acidic or basic inorganic medium, which in itself gives rise to additional costs due to reprocessing of the mother liquors and/or the salts formed in the course of the process.

When these molecules have to be produced in an optically active form, several strategies have been described and developed (Schurig et al. 1992, Pedragosa-Moreau et al. 1995). For example, the Katzuki-Sharpless oxidation reaction makes it possible to convert an olefin into an optically enriched epoxide by means of a titanium-based chiral organometallic catalyst. However, this approach is limited to olefins bearing an alcohol group in the alpha position of the double bond, necessary for coordination of the catalyst.

Other methods have been developed more recently, and they too are based for the most part on the use of organometallic catalysts very often involving heavy metals such as manganese or cobalt. However, although they are very effective on certain types of substrates, they only display average selectivities on other families of molecules. In all cases, they are difficult to use in industrial conditions, owing to the technical constraints imposed by the use of the heavy metals involved.

Various techniques of biocatalysis have been described for overcoming this problem. They employ indirect strategies involving the use of enzymes such as lipases, peroxidases or monooxygenases (Archelas et al. 1997). However, most of these approaches require the development of expensive systems for the recycling of cofactors, once again making them particularly difficult and expensive to implement in preparative conditions.

The use of an enzyme that makes it possible to effect direct hydrolysis of an epoxide therefore represents an interesting and original means of direct preparation of optically enriched epoxides or of achiral, racemic or optically enriched diols. These enzymes, called epoxide hydrolases, offer the advantage on the one hand of not requiring a cofactor and, on the other hand, of making it possible to effect the addition of a water molecule to an epoxide in particularly mild conditions. If the substrate is chiral, and depending on the enantioselectivity and the regioselectivity of this addition process, the diol obtained will be racemic or enantiomerically enriched (Archelas et al. 1998).

Although numerous works have been devoted to this type of enzyme present in mammals, their use in organic synthesis cannot be envisaged owing to the difficulty of obtaining them in sufficient quantity.

The possibility of using epoxide hydrolases of microbial origin (bacteria, yeasts, fungi)—which can be produced in large quantities by simple microbial fermentation—as a "tool" in organic synthesis would therefore constitute a considerable advance.

Examples of preparation of optically active compounds by using microorganisms as biocatalysts have been described, but only relate to uncharacterized enzymatic activities detected in various microorganisms. Thus, in European patent application EP 611 826 (Daicel Chemical Industries Co. Ltd.), the examples of microorganisms given, capable of producing an (S) optically active epoxide starting from a racemic epoxide, are in particular a strain of microorganism belonging to the genus *Candida, Rhodosporidium, Rhodococcus* and *Nosardioides*. The examples of microorganisms capable of producing an (R) optically active epoxide are, in particular, a strain of microorganism belonging to the genus *Thichosporon, Geotrichum, Corynebacterium, Micrococcus*, and *Brevibacterium*.

Styrene oxide is one of the test substrates finding widest application in studies conducted on mammalian epoxide hydtolases, and various derivatives substituted on the aromatic ring of this model substrate have also been investigated in this context (Dansette et al. 1978; Westkaemper et al. 1981). More recently, studies carried out with enzymatic activities of microbial origin have also used this model substrate, and the inventors themselves have shown that these molecules can be hydrolysed enantioselectively by a strain of the fungus *Aspergillus niger*, registered at the Natural History Museum (Paris) under No. LCP521 (Lab. de Cryptogamie, 12 rue Buffon, 75005 Paris, France) (Pedragosa-Moreau et al. 1996).

Nevertheless, experiments of enantioselective hydrolysis effected with the aid of fungi, such as the fungus *Aspergillus niger*, described up till now, make use of whole cells or of cellular extracts of the fungus, which creates a number of technical problems in application, does not give good yields, and does not allow the structure of the biological catalyst employed to be defined.

The use of well identified and characterized epoxide hydrolases of fungal origin would make it possible to remedy these drawbacks, but so far it has not been possible to isolate and purify an epoxide hydrolase of fungal origin, suggesting the possibility that such an enzyme would not be sufficiently stable to be completely isolated from its natural environment.

The present invention results from the demonstration, by the inventors, of the fact that it is possible to isolate and purify an epoxide hydrolase from fungi. Thus, the present invention follows from the identification (by purification, sequencing, cloning) of the enzyme responsible for the epoxide hydrolase activity of fungi, such as those of the *Aspergillus* species.

One of the aims of the present invention is to supply novel enzymes with epoxide hydrolase activity of fungal origin.

Another aim of the present invention is to supply the nucleotide sequences encoding these enzymes.

A further aim of the invention is to supply host cells transformed by the aforementioned nucleotide sequences, in which the said enzymes are advantageously overexpressed.

The invention also has the aim of supplying methods of obtaining the said enzymes, notably by extraction and purification from cells of fungi, or by culturing host cells as described above.

Another aim of the present invention is to supply novel methods of biocatalysis using the aforementioned enzymes or host cells that are producers of the said enzymes described above, for the synthesis of various epoxides and/or diols, and these methods give higher yields than the methods using whole cells, or cellular extracts of fungi previously described.

Accordingly, the invention aims more particularly to supply methods of hydrolysis of achiral or chiral epoxides offering the advantage that they can be carried out in particularly mild experimental conditions, i.e. without employing an organic or inorganic, acidic or basic reagent, notably in a buffered or unbuffered aqueous medium and/or in the presence of water-miscible or water-immiscible organic solvents. Depending on the intrinsic stereochemical properties of the starting epoxide, these methods result in the production of an achiral, racemic or optically enriched diol or—if the starting epoxide is chiral—in the production of one of its two enantiomers in optically enriched form, or even enantiomerically pure form.

The invention relates to any protein of fungal origin having epoxide hydrolase activity, such as is obtained in essentially pure form by extraction from cells of fungi, or by culture of host cells transformed by a nucleotide sequence coding for the aforementioned fungal protein, or to any protein derived by substitution, suppression or addition of one or more amino acids of the aforementioned protein of fungal origin and possessing epoxide hydrolase activity.

The aforementioned epoxide hydrolase activity can be measured using para-nitrostyrene oxide (pNSO) as substrate, and measuring the quantity of diol formed, notably according to the following method:

Add 50 μL of the preparation containing the enzyme to 410 μL of 0.1 M sodium phosphate buffer pH 7.0 (buffer B) and pre-incubate the mixture at 35° C. for 2 min. Then add 40 μL of a 50 mM solution of racemic pNSO in DMF (final pNSO concentration: 4 mM).

After 10 min of incubation, stop the reaction by adding 1 mL of dichloromethane. Stir the mixture vigorously so as to extract both the substrate and the diol produced. The quantity of diol formed is determined after separation on a column of silica by HPLC (high-pressure liquid chromatography) (Waters Associates, USA) as described previously (Nellaiah et al. 1996).

One unit of epoxide hydrolase represents the quantity of enzyme that catalyses the formation of one μmol of diol per minute in the above conditions. After incubation with raw extracts, the quantity of diol formed increases linearly with time for at least 30 min, and the reaction rate is proportional to the concentration of the enzyme in the range of 0.01 to 1.2 units (Nellaiah et al., 1996).

The invention relates more particularly to any protein as described above, characterized in that it comprises:

the sequence SEQ ID NO: 2.

or any sequence derived from the sequence SEQ ID NO: 2, notably by substitution, suppression or addition of one or more amino acids, and possessing epoxide hydrolase activity, the said derived sequence preferably having a homology of at least 40%, and especially above approx. 80%, with the sequence SEQ ID NO: 2, or any fragment of the sequence SEQ ID NO: 2, or a sequence derived from the latter as defined above, and possessing epoxide hydrolase activity, the said fragment preferably consisting of at least about 10 amino acids that are contiguous in the region delimited by the amino acids situated at positions 1 and 339 of the sequence SEQ ID NO: 2.

The invention relates more particularly to any protein described above, characterized in that it corresponds to a fungal epoxide hydrolase in essentially pure form, such as is obtained by extraction and purification from cultures of cells of fungi of the *Aspergillus* species.

Accordingly, the invention relates more particularly to any aforementioned protein, characterized in that it corresponds to the fungal epoxide hydrolase in essentially pure form represented by SEQ ID NO: 2, such as is obtained by extraction and purification from cultures of cells of strains of *Aspergillus niger* or of *Aspergillus turingensis*.

The invention also relates to any protein as described above, characterized in that it corresponds to a recombinant fungal epoxide hydrolase such as is obtained in essentially pure form by transformation of suitable host cells by means of vectors containing:

the nucleotide sequence SEQ ID NO: 1 encoding the epoxide hydrolase represented by SEQ ID NO: 2, or any sequence derived from SEQ ID NO: 1 by degeneration of the genetic code, and encoding the epoxide hydrolase represented by SEQ ID NO: 2, or any sequence derived from the sequence SEQ ID NO: 1, in particular by substitution, suppression or addition of one or more nucleotides, and coding for an enzyme possessing epoxide hydrolase activity, the said derived sequence preferably having a homology of at least about 45%, and especially above about 80%, with the sequence SEQ ID NO: 1, or any fragment of the sequence SEQ ID NO: 1, or of a sequence derived from the latter as defined above, and coding for an enzyme possessing epoxide hydrolase activity, the said fragment preferably consisting of at least about 20 nucleotides that are contiguous in the region delimited by the nucleotides situated at positions 1 and 1197 of the sequence SEQ ID NO: 1.

Accordingly, the invention relates more particularly to the recombinant fungal epoxide hydrolase represented by SEQ ID NO: 2, such as is obtained by transformation of suitable host cells by means of vectors containing the nucleotide sequence SEQ ID NO: 1, or any sequence derived from SEQ ID NO: 1 by degeneration of the genetic code, and encoding the epoxide hydrolase represented by SEQ ID NO: 2.

The invention also relates to any nucleotide sequence encoding a protein of fungal origin with epoxide hydrolase activity as defined above.

The invention relates more particularly to any aforementioned nucleotide sequence, characterized in that it comprises:

the sequence represented by SEQ ID NO: 1 encoding the epoxide hydrolase represented by SEQ ID NO: 2, or any sequence derived from the sequence SEQ ID NO: 1 by degeneration of the genetic code, and encoding the epoxide hydrolase represented by SEQ ID NO: 2, or any sequence derived from the sequence SEQ ID NO: 1, especially by substitution, suppression or addition of one or more nucleotides, and encoding an enzyme possessing epoxide hydrolase activity, the said derived sequence preferably having a homology of at least about 45%, and especially above about 80%, with the sequence SEQ ID NO: 1, or any fragment of the sequence SEQ ID NO: 1, or of a sequence derived from the latter as defined above, and encoding an enzyme possessing epoxide hydrolase activity, the said fragment preferably being constituted of at least about 20 nucleotides that are contiguous in the region delimited by the nucleotides situated at positions 1 and 1197 of the sequence SEQ ID NO: 1, or any complementary nucleotide sequence of the aforementioned sequences or fragments, or any nucleotide sequence encoding an enzyme possessing epoxide hydrolase activity, and capable of hybridization with one of the aforementioned sequences or fragments, the aforementioned sequences or fragments being in the single-stranded or double-stranded form.

The invention also relates to any vector, especially plasmid, containing a nucleotide sequence as defined above.

Advantageously, the nucleotide sequences of the invention in the aforementioned vectors, are put under the control of elements that regulate the expression of the proteins with epoxide hydrolase activity defined above, notably a promoter, inducible if necessary, and a transcription terminator.

Preferably, the aforementioned promoter is selected from those that permit overexpression of the said proteins in the host cells transformed by means of the vectors, the said host cells themselves being selected from those that are able to overexpress the said proteins, especially among the bacteria, viruses, yeasts, fungi, plants or mammalian cells.

The invention also relates to any host cell, selected in particular from bacteria, viruses, yeasts, fungi, plants or mammalian cells, the said host cell being transformed, notably by means of a vector as defined above, in such a way that its genome contains a nucleotide sequence as mentioned above encoding a protein with epoxide hydrolase activity.

The invention also relates to the use of proteins with epoxide hydrolase activity as defined above, as enzymatic biocatalysts in the implementation of methods of preparation of epoxides or of enantiomerically pure vicinal diols, especially in the pharmaceutical and plant-protection field, or in the manufacture of specific optical materials.

Accordingly, the invention relates more particularly to a method of preparation of epoxides and/or of enantiomerically pure diols respectively of the following formulae (II) and (III)

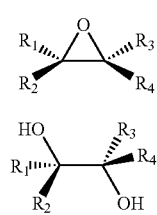

in which $R_1$, $R_2$, $R_3$ and $R_4$ represent any groups, and especially groups that are characteristic of pharmaceutical and plant-protection compounds, or of specific optical materials corresponding to the said epoxides or vicinal diols, the said method comprising a stage of treatment of a mixture of diastereoisomeric epoxides, or of a chiral epoxide in racemic form, or of a prochiral epoxide of the following formula (I):

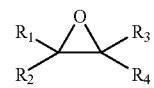

with a protein with epoxide hydrolase activity as defined above, or with host cells as mentioned above, expressing or overexpressing a protein with epoxide hydrolase activity as defined above, which leads to the production of:

a mixture of the aforementioned compounds of formulae (II) and (III), it being possible, if necessary, for the said compounds of formula (II) and (III) to be separated by an additional stage of purification, or just the compound of the aforementioned formula (III).

In the case of production of just the compound of the aforementioned formula (III), this can be effected by a treatment that accompanies or is subsequent to the treatment described above, notably with another chemical or enzymatic reagent depending on the starting epoxide, for example with sulphuric acid, especially in the case of para-nitrostyrene oxide (Pedragosa-Moreau et al., 1997), or with cells of the fungus *Beauveria sulfurescens*, especially in the case of styrene oxide (Pedragosa-Moreau et al., 1993).

Advantageously, when the method as described above according to the invention is carried out by means of a protein with epoxide hydrolase activity as defined above, the latter can be immobilized on a solid support such as DEAE cellulose or DEAE Sepharose, or any other support or technique that makes it possible to immobilize this enzyme.

The invention also relates more particularly to the use of a protein with epoxide hydrolase activity as defined above, in various forms, including transformed host cells as described above, or of whole cells of fungi, such as *Aspergillus niger*, producing this enzyme, or soluble or freeze-dried enzymatic extracts of the said cells, or the enzyme immobilized on a solid support as defined above, in the implementation of a method as described above for hydrolysis of an achiral epoxide.

The invention also relates to a method of preparation of protein with recombinant epoxide hydrolase activity as defined above, characterized in that it comprises a stage of transformation of host cells, preferably selected from bacteria, viruses, yeasts, fungi, plants or mammalian cells, with a vector as described above, and a stage of purification of the recombinant epoxide hydrolase produced by the said cells.

The invention also relates to a method of preparation of a fungal epoxide hydrolase in essentially pure form, the said method comprising:

a stage of extraction of the enzyme from cell cultures of fungi, such as fungi of the *Aspergillus* species, notably by crushing the fungus using a French press or any other suitable means, followed by a stage of low-speed centrifugation (approx. 10 000 g), recovery of the supernatant, and concentration by ultrafiltration.

a stage of purification of the enzyme from the extract obtained in the preceding stage, notably by successive passages through columns of DEAE-Sepharose, Phenyl-Sepharose, Mono Q and Superose 12.

The invention will be further illustrated by the following description of the purification of the epoxide hydrolase from a strain of the fungus *Aspergillus niger*, as well as cloning of the gene encoding this epoxide hydrolase, and examples of application of a method according to the invention.

A) Purification and Characterization of an Epoxide Hydrolase from *Aspergillus niger* with High Enantioselectivity

1) Equipment and Methods

1) Reagents

The test substrate used is racemic p-nitrostyrene oxide (pNSO). It is synthesized from ω-bromo-4-nitro acetophenone according to a technique described by Westkaemper and Hanzlik, 1980. Its pure (R) and (S) enantiomers are obtained from this racemic substrate by a stage of biotransformation (Pedragosa-Moreau et al., 1996). Diethylaminoethyl (DEAE)-Sepharose, phenyl-Sepharose, the "Mono Q" and Superose 12 columns are obtained from Pharmacia LKB (Uppsala, Sweden). $H_2[^{18}O]$ is obtained from Isotec (Miamisburg, USA) and its $[^{18}O]$ content is 95%. All the protein chromatography is effected using the FPLC Pharmacia system at 4° C.

2) Organisms, Conditions of Growth and Preparation of Extracts

The strain of the fungus *Aspergillus niger* used in this study is registered at the Natural History Museum (Paris) under No. LCP521 (Lab. de Cryptogamie, 12 rue Buffon, 75005 Paris, France). Culture is carried out in a fermenter with a capacity of 5 L (liquid volume) in the conditions described by Nellaiah et al., 1996. The cells are harvested after 40 h of culture by filtration. They are suspended in 10 mM Tris-HCl buffer of pH 7.1 (buffer A) containing 1 mM cysteine, 1 mM EDTA and 0.3 mM phenylmethane sulphonyl chloride (PMSF). An acellular extract is prepared by crushing the fungus using a French press, or any other means that can be used by a person skilled in the art, and low-speed centrifugation (1000 g) in the conditions described by Nellaiah et al., 1996. This extract is concentrated at 100 mL by tangential-flow filtration using a membrane with a cutoff threshold of 10, 40 or up to 100 kDa. Any other manipulation is carried out at a temperature of 4° C. in a buffer solution containing 1 mM cysteine, 1 mM EDTA and 0.3 mM PMSF to avoid inactivating the enzyme. The concentration of the protein is determined by the method of Lowry et al., 1951, using bovine serum albumin as reference.

3) Purification of the Epoxide Hydrolase

The concentrated solution containing the enzyme is deposited on a column of DEAE (diethylaminoethyl)-Sepharose (2.5 cm×30 cm) previously equilibrated with buffer A containing 0.13 M KCl. The column is washed with 360 mL of equilibrating buffer, and elution is carried out with a linear gradient of 0.13–0.23 M KCl in buffer A (total volume: 510 mL, flow rate: 3 mL/min, volumes of the fractions: 6 mL).

The activity is eluted for a potassium chloride concentration of 0.17–0.20 M. The active fractions are combined and concentrated to 5 mL by ultrafiltration. The concentrate is deposited on a column of phenyl-Sepharose (1 cm×10 cm), previously equilibrated with buffer A containing $(NH_4)_2SO_4$ 0.25 M and 21% (v/v) of ethyleneglycol. The column is washed with 10 mL of the same buffer, and elution is carried out with a linear gradient of ethyleneglycol of 21–56% (v/v) in buffer A containing $(NH_4)_2SO_4$ 0.25 M (total volume: 95 mL, flow rate: 0.5 mL/min, volumes of the fractions: 1 mL).

The activity is eluted with an ethyleneglycol concentration of 30–43% (v/v). The active fractions are combined and concentrated to 5 mL. The concentrate is deposited on a Mono Q column (0.5 cm×5 cm), previously equilibrated with Tris-HCl buffer 10 mM, pH 6.5, containing 0.13 M KCl. The column is washed with 5 mL of buffer, and elution is carried out with a linear gradient of potassium chloride of 0.13–0.25 M (total volume 85 mL; flow rate 0.5 mL/min; volumes of the fractions: 1 mL). The activity is eluted to a concentration of 0.15–0.16 M of potassium chloride. The active fractions are combined and concentrated to 1 mL. The solution containing the enzyme (200 mL) is deposited on a column of Superose 12 (1 cm×30 cm) and equilibrated with buffer A (flow rate 0.3 mL/min; volumes of the fractions: 0.6 mL). This stage is carried out 5 times (200 μL each time) and all the active fractions are combined. The preparation thus obtained is stored at 4° C.

4) Enzymatic Study

The incubations with $H_2[^{18}O]$ are carried out in 1 mL flasks containing 180 μL of $H_2[^{18}O]$ buffer B, 20 μL of the purified epoxide hydrolase and 20 μL of substrate (50 mM in acetonitrile). After 1.5 h of incubation at 25° C. with magnetic stirring (500 rpm) the substrate that remains and the product formed are extracted with 2 mL of dichloromethane. The diol is purified by analytical chromatography on silica (eluent: diethylether). 2 μL of samples are analysed by gas chromatography/mass spectrometry (GC/MS). The diol that remains is converted to the corresponding acetonide by reaction with 2,2-dimethylpropane in the presence of p-toluene sulphonic acid. The acetonide is analysed by GC/MS as already described by Audier et al., 1968.

Reaction in a total volume of 5 mL is carried out at 25° C., with a substrate with a concentration of 4.3 mM with DMSO (20 vol.%) as co-solvent in a 0.1 M sodium phosphate buffer pH 8.0.

The reaction is started by adding 13 U/L of the purified enzyme. Samples are taken every 30 minutes for quantification of the concentrations of the substrate and of product by HPLC using a reversed-phase column (Nellaiah et al., 1996) and for quantification of the enantiomeric excess of the epoxide and of the diol by gas-phase chromatography (Nellaiah et al., 1996).

5) Polyacrylamide Gel Electrophoresis

SDS-PAGE electrophoresis is carried out on a plate with thickness of 1 mm containing a resolving gel (10% of acrylamide) and a concentrating gel (4% of acrylamide) at pH 8.8 in the presence of 0.1% of sodium dodecyl sulphate (SDS) (Laemmli, 1970). The samples are dissolved in a Tris-HCl buffer (62.5 mM, pH 8.8) containing 1% (w/v) of SDS, 10% (v/v) of glycerol and 2% (v/v) of β-mercaptoethanol, and are heated at 100° C. for 2 minutes. The proteins are stained with 0.1% (w/v) of Coomassie blue. Migrations on non-denaturing PAGE gels were effected in the same way except that no β-mercaptoethanol was added to the resolving buffer, and that the samples were not heated. Electrofocusing was carried out with a pH gradient of 3–9 by means of the Pharmacia LKB "Phastsystem" system and standard Pharmacia procedures. The proteins were stained with silver nitrate.

6) Determination of Molecular Weight

The molecular weight was estimated after SDS-PAGE by comparing the mobility (Rf) of the purified epoxide hydrolase (EH) with that of the following reference proteins: phosphorylase B (97.4 kDa), bovine serum albumin (66.2 kDa), ovalbumin (45 kDa), carbonic anhydrase (31 kDa), trypsin inhibitor (21.5 kDa) and lysozyme (14.4 kDa). The molecular weight of the native enzyme was estimated from the elution profile of Superose 12 by comparing the Kav of the purified EH with that of the following standard proteins: alcohol dehydrogenase (150 kDa), bovine serum albumin (67 kDa), ovalbumin (43 kDa), chymotrypsinogen A (25 kDa) and ribonuclease A (13.7 kDa). The exclusion volume and the dead volume were determined using dextran blue and vitamin B12.

7) Amino Acid Sequence

For the amino acid analyses and the N-terminal sequence determinations, the peptides were transferred from the SDS gels onto a "glassy-bond" membrane (Biometra, Germany) using standard Biorad procedures (Hercules, USA). The amino acid composition of the enzyme was determined after acid hydrolysis (6 N HCl at 100° C. under vacuum for 24 h) using an automatic amino acid analyser (Beckman 6300 system, Germany). The molecular weight was estimated from the amino acid composition using Delaage's method (1968).

8) Peptide Sequences

The proteins were dissolved in an SDS buffer and separated by SDS-PAGE. Part of the gel was stained with Coomassie Blue, and the strip of interest was separated from the rest of the gel. The strip was washed for 1 h with $H_2O$, $H_2O$—$CH_3OH$ (90:10), $H_2O$—$CH_3CN$ (80:20), and $H_2O$—$CH_3CN$ (50:50). The strip of gel was then cut into small pieces and dried under vacuum in a Speed-Vac (Savant). Next, 400 µL of a solution containing 25 mM Tris-HCl (pH 8.5), 1 mM EDTA, 0.05% SDS, and 5 µg of the protease Lys-c (Boehringer Mannheim) was added, and the mixture was incubated overnight at 37° C. The hydrolysate was injected into a reversed-phase HPLC column (Vydac $C_{18}$; 2.1×250 mm). The column was eluted at a flow rate of 0.2 mL/min with a linear gradient of 0 to 35% of solution B ($CH_3CN$, containing 0.07% of trifluoroacetic acid) for 150 min (solution A consists of water and 0.07% of trifluoroacetic acid) and the peaks were collected and sequenced directly with an Applied Biosystems model 477A microsequencer.

9) PCR Reaction, Cloning and Sequencing

The PCR reactions were carried out using degenerated oligomers obtained from partial amino acid sequences as primer and using the genomic DNA of *Aspergillus niger* as support. The genomic DNA was extracted from 1.5 g of mycelium washed with water, ground in liquid nitrogen and suspended in buffer Tris-HCl 50 mM pH 7.5, EDTA 50 mM, SDS 3%, β-mercaptoethanol 1%. After reaction for 1 h at 65° C., the solution was extracted with a phenol/chloroform/isoamyl alcohol mixture (24/24/1, v/v/v) and chloroform/isoamyl alcohol mixture (24/1), precipitated with isopropanol, and the sediment was dissolved in TE buffer (Tris-HCl 10 mM pH 7.5 and EDTA 1 mM). RNase was added (30 µg/mL) in the course of 1 h at 37° C., the DNA was precipitated with isopropanol, washed in 70% ethanol and dissolved in water. The PCR reactions were carried out in a total volume of 50 µL, using 100 ng of DNA, dNTP 200 µM, each primer at 2 µM and 2 units of Taq polymerase (Perkin Elmer). The PCR reactions were effected by heating at 95° C. for 5 min, then carried out for 30 cycles of amplification at three temperatures (1 min at 95° C., 1 min at 58° C., and 1 min at 72° C.). The amplified fragments were cloned at the ECOR V site of pBluescript II SK(-) (Statagene) after treatment with one unit/µL of terminal transferase (Boehringer). The fragments were sequenced using a Pharmacia T7 sequencing kit.

II) Results

The EH from *Aspergillus niger* was purified to electrophoretic homogeneity using a 4-stage chromatographic procedure. In total, 120 µg of the purified enzyme was prepared starting from 24 g of dry mycelium, i.e. from 5 L of culture medium. These relatively low values are due to 2 reasons:

1) the overall (total) yield is low (4%) on account of the instability of the enzyme during the purification procedure mainly in the stages of concentration by ultrafiltration when the concentration of the protein is low;

2) the initial content of EH in the cellular extract of *Aspergillus niger* is low: a value of 0.4% of the soluble proteins is calculated using the specific activity of the purified enzyme. However, the purified enzyme is responsible for all of the activity of the fungus on pNSO. Thus, there is probably only one active protein on this substrate in *Aspergillus niger*.

The purified epoxide hydrolase (EH) has a single band in native PAGE or SDS gel after staining with Coomassie Blue. Determinations of the activity of slices of gel obtained after electrophoresis of a non-denaturing polyacrylamide gel reveal a single band located at the same level as the band of the labelled protein. The isoelectric point of the protein is 4.5 after determination by electrofocusing using a pH gradient from 3 to 9 and silver nitrate staining.

The EH of *Aspergillus niger* is a tetramer made up of four identical subunits of 45 kDa. The EHs from other sources are generally monomeric or dimeric proteins. However, the epoxide hydrolase of Corynebacterium sp. has recently been described as being dodecameric (Misawa et al., 1998).

The effect on the activity of several selective reagents was tested. EDTA and PMSF show no effect. Oxidizing agents such as meta-chloroperbenzoic acid or hydrogen peroxide strongly inhibit the activity of the enzyme. On the other hand, reducing agents such as β-mercaptoethanol or cysteine show a positive effect on the enzyme's activity. Moreover, strong inactivation is observed with thiol blocking agents such as $HgCl_2$, 4-hydroxy-mercuribenzoate, iodoacetamide or dithionitrobenzene (DTNB). All these results demonstrate the essential role of one or more cysteine residue(s) on the activity of epoxide hydrolase. A similar effect is observed with the soluble EHs (sEH) from mammals (Wixtrom et al., 1985) and with the EH from *Pseudomonas sp*. (Rink et al., 1997), whereas the microsomal EHs (mEH) from mammals (Wixtrom et al., 1985) are not sensitive to thiol reagents.

The pH activity profile and the inhibition by ω-bromo-4-nitro acetophenone suggest the participation of a histidine residue in the catalytic mechanism. Moreover, certain cysteine residues are important for the activity of the enzyme as demonstrated for mammalian sEH but not for mEH (Wixtrom et al., 1985). The catalytic mechanism of mammalian sEH and mEH for the hydrolysis of epoxides has recently been elucidated (Beetham et al., 1995; Arand et al., 1996). A two-stage mechanism involving the formation of an intermediate covalent ester has been demonstrated with the participation of two aspartic acids and one histidine residue. However, little is known about the catalytic mechanism of microbial EHs. Recently, a similar mechanism was demonstrated for the epoxide hydrolase of the bacterium *Agrobacterium radiobacter* (Rink et al., 1997). These elements suggest that the EH of *Aspergillus niger* uses a similar mechanism for the hydration of epoxides as the mammalian EHs. This mechanism accords with the general process of catalysis demonstrated for the hydrolysis of para-substituted styrene oxide by a raw extract from *Aspergillus niger* (Pedragosa-Moreau et al., 1996).

With pNSO, addition of an organic solvent is required for dissolving the substrate. In fact, in the absence of co-solvent, no activity can be detected. It was shown for other soluble EHs that they were not active on micellar substrates (Hammock et al., 1997). Thus, the effect of different co-solvents on the activity of epoxide hydrolase from *Aspergillus niger* was investigated. The nature of the co-solvents has a considerable influence on the yield in opening of the epoxide, the strongest activities being obtained for DMF and acetone. The low activity obtained with THF could be correlated with inactivation of the enzyme by traces of peroxides that are usually present in the solvent.

The enzyme is active at a pH ranging from 5 to 9 with a maximum peak at pH 7. The enzyme is active at a temperature ranging from 2 to 45° C. with a maximum activity at 40° C. From 2 to 40° C. the activity increases slightly (only 4 times) as indicated by the low activation energy (27 kJ.mol$^{-1}$.° K$^{-1}$).

From the practical standpoint, the EH from *Aspergillus niger* is very interesting for organic synthesis on account of its ability to hydrolyse racemic epoxides in a highly enantioselective manner. The enantioselectivity is due to a higher affinity and a higher catalytic constant for the (R) enantiomer of pNSO relative to the (S) enantiomer.

The ratio of the specific constant ($k_{cat}$/Km) shows that the initial rate of hydrolysis of the (R) enantiomer is 55 times faster than that of the (S) enantiomer starting from racemic pNSO. This result is similar to that obtained with whole cells on the same substrate (Pedragosa-Moreau, 1997). Moreover, the regioselectivity of the reaction is very high: 97% for the 2 carbon, as shown with the whole fungus (Pedragosa-Moreau, 1996). The enantioselectivity and the regioselectivity of hydrolysis of pNSO by the purified EH of *Aspergillus niger* are very similar to those determined with all of the cells. Accordingly, the purified enzyme is responsible for the entire activity of the fungus on pNSO.

B) Cloning and Characterization of the Soluble Epoxide Hyrolase from *Aspergillus niger* Which is Related to Mammalian Microsomal Epoxide Hydrolases I) Experimental Procedure 1) Isolation of Nucleic Acids from *Aspereillus niger* (*A. niger*)

*Aspergillus niger* (the aforementioned strain No. LCP 521) was cultivated in a medium containing 10 g of glucose and 20 g of maize liquor (Sigma, St. Louis, Cat. No. C4648) per litre of culture. Incubation was effected in a volume of 100 ml in a flask agitated at 28° C. for 3 days after inoculation with spores of the fungus. The mycelium is harvested by filtration on cloth and stored at −70° C. after determination of the wet weight. Extraction of RNA is carried out by the method of Chomczynski and Sacchi (1986) using 10 mL of denaturing solution per gram of mycelium. The typical yield is 300 µg of total RNA per gram of mycelium. For isolation of the RNA, 2 g of mycelium is homogenized with a Potter type of glass homogenizer in 15 mL of a lysis solution (solution of guanidine hydrochloride 6 M, containing 0.1 M of sodium acetate, pH 5.5). After centrifugation at 10,000 g for 10 min, the supernatant is transferred to another tube and 2.5 volumes of ethanol are added. The precipitated nucleic acids are collected by centrifugation at 10,000 g for 10 min and the resulting residue is dissolved overnight in 10 mL of lysis buffer after brief drying. The insoluble fraction is removed by centrifugation and the nucleic acids are precipitated again by adding 25 mL of ethanol. The centrifugation pellet is washed with 70% ethanol, dried in air for 30 min and dissolved in a TE buffer, pH 8.0.

2) Cloning of the Gene of the EH of *Aspergillus* and of cDNA by the Polymerase Chain Amplification Technique (Polymerase Chain Reaction, PCR)

The reverse PCR for amplification of the gene of the *Aspergillus* EH was effected according to the following scheme: 500 ng of genomic DNA is digested with a suitable restriction enzyme (most of the successful results are obtained with BamHI or Cfol) and are recovered by precipitation with ethanol after extraction with phenol/chloroform mixture. Of this 500 ng, 100 ng is circularized by ligation with DNA ligase T4 (Life Technologies) in a volume of 20 µL in the conditions specified by the supplier. One microlitre of the resulting preparation was amplified by PCR effected for 30 cycles (1 min 94° C., 1 min 60° C., 3 min 72° C.) with a DNA polymerase Taq (Perkin Elmer) in the standard reaction conditions recommended by the supplier. The primers used (MA226 5'-ATGCGATCGGACTGCTGGACA-3'    SEQ ID NO: 3 and

MA227 5'-CGCGGGCAATCCACACCTAC-3')    SEQ ID NO: 4 are deducted from the sequence of a genomic fragment obtained previously. An XhoI restriction site located between the two priming sites in the genomic sequence is used optionally for relinearizing the circular DNA before the reverse PCR, in order to suppress the torsional stress and so improve the efficiency of initial amplification of the genomic support. The PCR products are separated by electrophoresis on agarose gel and the specific amplicons of the EH of *Aspergillus* are identified by immunotransfer according to the Southern technique using the aforementioned genomic fragment as a probe. The fragments of *Aspergillus* EH gene identified in this way are purified by electrophoresis on agarose gel using the Quiaex kit (Qiagen), and cloned in the pGEM-T vector (Promega) for sequence analyses by the chain termination method.

On the basis of the information obtained from the sequence, 2 primers (MA2905'-cggaattccATGgTCACTGGAGGAG-
CAATAATTAG-3' AND                    SEQ ID No:5

MA2915'-ttgaatTCCTACTTCTGCCACAC-3'    SEQ ID No: 6;

the residues in capital letters are complementary to
the support sequence)

surrounding the region encoding the protein of the EH gene are deducted and used for amplifying the respective fragments of the genomic DNA and for reverse-transcribing the mRNA with high fidelity DNA polymerase Pfu ("Stratagene") for 40 cycles (1 min 94° C., 1 min 50° C., 6 min 72° C.). The resulting DNA fragments are digested with EcoRI and inserted in pUC19 (New England Biolabs) for final sequence analysis.

3) Expression, Purification and Analysis of Recombinant Epoxide Hydrolase

For recombinant expression in *E. coli*, the cDNA fragment of the epoxide hydrolase of *Aspergillus* is amplified with a DNA polymerase Pfu using the primer MA291 (see above) and the primer MA318

5'gctgaattcacATGTCCGCTCCGTTCGCCAAG-3')    SEQ ID No: 7 in order to introduce an AflIII NcoI-compatible recognition site (underlined in primer MA318) in the probable initiation codon of the epoxide hydrolase gene of *Aspergillus* which was revealed by sequence analysis.

The pGEF+ bacterial expression vector is modified by introducing a multiple cutting site (5'-CCATGGGAATTCTCGAGATCTAAGCT-
TATGCATCAGCTGCATGG-3')    SEQ ID No: 8 in the NcoI site that contains the starting codon of the pGEF+ vector in the context adapted to a ribosome binding site, upstream of the promoter of the RNA polymerase T7. The resulting plasmid is called pGEF II hereinafter. The PCR fragment AflIII/Eco RI of the EH of *Aspergillus* is ligated in the NcoI/Eco RI site of pGEF II to produce the pGEF Asp EH" expression construction. The *E. coli* strain BL21 (DE 3) (Novagen) is transformed with pGEF Asp EH and put in the LB medium at 30° C. In late exponential phase, induction of expression of the recombinant protein is effected by adding isopropyl-β-thiogalactoside (100 µM). After two hours, the bacteria are collected by centrifugation, resuspended in 0.02 volumes of culture of the STE buffer (Tris-HCl, 10 mM, sodium chloride 100 mM, ethylenediamine tetraacetic acid 1 mM, pH 7.4) and stored at −70° C. Enzymatic activity is determined by converting the R enantiomer of para-nitrostyrene oxide to the corresponding diol. The reaction is carried out at a substrate concentration of 880 µM in 500 µL STE at 37° C. for 30 min, in the presence of 10 µL of acetonitrile which is used as solvent of para-nitrostyrene oxide.

The conversion reaction is terminated by extraction of the substrate with an equal volume of chloroform. In these conditions, more than 99.9% of the substrate is extracted in the organic phase and 60% of the diol is recovered in the aqueous phase.

The conversion substrate is quantified by adding 400 µL of supernatant to 800 µL of water and reading the optical density at 277 nM, with the molar extinction coefficient of the product being $9.1 \times 10^3$ $M^{-1}$ $cm^{-1}$. The epoxide hydrolase of *Aspergillus* is purified to homogeneity by a three-stage procedure, according to the method described above.

Antibodies directed against the purified protein were obtained by immunizing rabbits according to the technique described by Friedberg et al., 1991. The purified protein is analysed by SDS polyacrylamide gel electrophoresis followed by labelling with Coomassie Blue or by immunotransfer in accordance with the procedures published previously.

4) Construction and Analysis of Epoxide Hydrolase Mutants

PCR-controlled, directed mutagenesis of the cDNA of epoxide hydrolase of *Aspergillus* is carried out by the method of Tomic et al., 1990, as described previously for soluble mammalian epoxide hydrolases and microsomal epoxide hydrolases (Arand et al., 1996; Arand et al., 1999).

Primers were used for introducing various mutations. The mutations affecting the catalytic nucleophile $Asp^{192}$ were introduced by replacing the NcoI internal cassette of the cDNA of the epoxide hydrolase of *Aspergillus* with the PCR-modified fragment.

In addition, mutations targeting the residues of the charge relay system, namely $Asp^{348}$ and $His^{374}$, are introduced by replacing an XhoI fragment with the respective PCR fragment. The PCR modifications are generated using DNA polymerase Pfu so as to minimize the introduction of unwanted sequence modifications. All the PCR-generated fragments are finally sequenced to ensure they are correct. After recombinant expression, the solubility of the mutant proteins is tested, which represents an indicator of their structural integrity. After sonication of the bacterial sediments, the resulting suspension is centrifuged at 10,000 g, the pellet and the supernatant are tested for presence of the epoxide hydrolase of *Aspergillus* by immunotransfer. The enzymatic activity is tested in the supernatant as described previously.

II) Results

Isolation of the gene of epoxide hydrolase (EH) of *Aspergillus* and the cDNA by reverse PCR, were obtained. It was difficult to obtain specific amplified fragments using restriction enzymes with the hexameric recognition sites for digestion of the genomic DNA.

This seems to be due to two pairing errors in the MA226 primer, in comparison with the sequence of natural origin, which weakens the amplification of the long products, but poses no problem when using restriction enzymes with tetrameric recognition sequences. However, the first fragment obtained after restriction by BamHI of the DNA seems to be artificially truncated, which is a consequence of the internal priming of the initial amplicon. In consequence, the 3' region of the EH of *Aspergillus* downstream from the genomic sequence is lacking in this fragment and must be obtained separately in a second reverse PCR experiment.

The epoxide hydrolase of *Aspergillus* is evidently related to the mEHs of mammals, although this enzyme is unique in several respects.

First, it is a soluble enzyme that does not have an anchoring sequence in the membrane, in contrast to the microsomal epoxide hydrolases of mammals (mEHs), and their corresponding enzymes in the arthropods.

Second, the EH of *Aspergillus* has a much higher conversion power with para-nitrostyrene oxide, than that of mammalian epoxide hydrolases with their substrates.

Whereas the rat microsomal epoxide hydrolase (mEH) has a specific activity with its model substrates styrene oxide and benzo[α]pyrene oxide of about 500 nmol converted per minute and milligram of pure enzyme, the epoxide hydrolase of *Aspergillus* hydrolyses 100 µmol of 4-nitro-styrene oxide per minute and milligram of enzyme. The conversion number of rat mEH was increased by a factor of 30 by replacing the acid residue of the charge relay system of its catalytic site, i.e. $Glu^{404}$, with aspartic acid. Interestingly, the corresponding residue in the native *Aspergillus* epoxide hydrolase is already an aspartic acid, in contrast to the fact that glutamic acid occupies this position in all the other mEH enzymes. Substitution of catalytic $Asp^{348}$ in the epoxide hydrolase of *Aspergillus* by Glu leads to a moderate decrease of Vmax by a factor of just 2. At the same time, the $K_M$ fell by a factor of 3. A possible explanation of this observation might be a reversal in the stage limiting the degree of conversion of the enzymatic reaction. In the mEH and sEH of mammals the second hydrolytic stage of the enzymatic reaction seems to be a stage limiting the degree of conversion. In such conditions, i.e. when the rate constant of formation of the intermediate ester $k_1$ is much greater than the constant $k_2$ for the hydrolytic stage, the decrease in Vmax due to a reduced $k_2$ occurs in parallel with a similar decrease of $K_M$, because $K_M = K_D k_2/(k_1 + k_2)$. However, if, initially $k_1$ limits the degree, and $k_2$ is much greater, the expression $k_2/(k_1 + k_2)$ will be approximately equal to 1 and $K_M$ is equal to $K_D$. A halving of Vmax due to modulation of the charge relay system, i.e. of the important part of the catalytic site for the second stage of the enzymatic reaction, is probably due to a large decrease in $k_2$ of up to half the value of $k_1$. Consequently, $k_2/(k_1 + k_2)$ would now be close to ⅓, i.e. exactly the value observed for the $Asp^{348}$ Glu mutant of the epoxide hydrolase (EH) of *Aspergillus*. Thus, these results are compatible with the fact that in the case of EH of *Aspergillus* with para-nitrostyrene oxide as substrate, $k_2$ is greater than $k_1$, a situation that no longer exists in substitution of $Asp^{348}$ by Glu. This would correspond exactly to the scenario observed with the mEHs of mammals.

The structure of the gene of the epoxide hydrolase of *Aspergillus* is very complex, compared with the simplicity of the original organism. Whereas the average size of the introns identified is approx. 60 pb, and therefore in agreement with that of many other genes of *Aspergillus*, in contrast the number of introns in the *Aspergillus* gene, 8 in all, is abnormally high.

None of the exons/introns is conserved between fungi and mammals, despite the identical number of introns in the 2 organisms. The fungus and mammal genes both have a first non-coding exon. In the rat, the existence of at least 3 alternatives for the first exon has been noted. Here, the first non-coding exon permits the alternative use of different promoters for the synthesis of identical proteins.

C) EXAMPLES OF APPLICATION

Example 1

15 g of 1,1-diethoxybut-3-ene oxide (94 mmol or a concentration of 0.3 mol per litre of reaction medium) is added to 300 ml of phosphate buffer (pH 8, 0.1 M). The temperature is adjusted to 4° C. and 1.2 g of purified (native) enzyme is added. After stirring for 30 hours at 4° C., the residual epoxide is extracted with pentane. Evaporation of the solvent followed by distillation makes it possible to isolate 4.5 g of (S)-epoxide (yield=30%, ee=98%). Continuous extraction of the aqueous phase with dichloromethane makes it possible to isolate, after purification on a silica column, 9 g of (R)-diol (yield=54%, ee=47%).

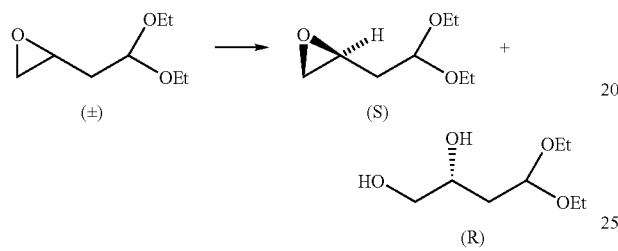

Example 2

6 g of para-bromo-α-methylstyrene oxide (28 mmol or a concentration of 0.35 mol per litre of reaction medium) is added to 75 ml of phosphate buffer (pH 8, 0.1 M). The temperature is adjusted to 4° C. and 0.35 g of purified (native) enzyme is added. After stirring for 8 days at 0° C. the residual epoxide is extracted with pentane. Evaporation of the solvent followed by distillation makes it possible to isolate 2.3 g of (S)-epoxide (yield=39%, ee=99.7%). Continuous extraction of the aqueous phase with dichloromethane makes it possible to isolate, after purification on a silica column, 3.19 g of (R)-diol (yield=49%, ee=96%).

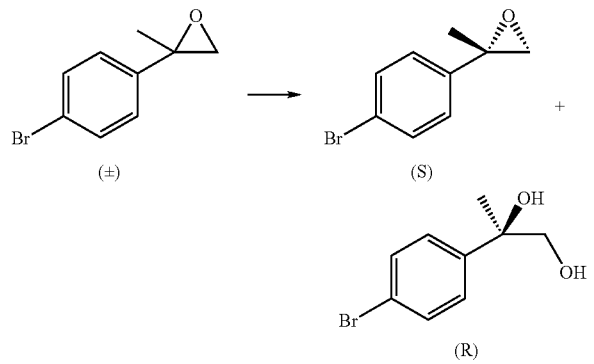

Example 3

4 g of para-chlorostyrene oxide (26 mmol or a concentration of 2 mol per litre of reaction medium) is added to 9 ml of phosphate buffer (pH 7, 0.1 M). The temperature is adjusted to 0° C. and 2.3 g of purified (native) enzyme is added. After stirring for 8 hours at 0° C. the residual epoxide is extracted with pentane. Evaporation of the solvent followed by distillation makes it possible to isolate 1.9 g of (S)-epoxide (yield=47%, ee=99%). Extraction of the aqueous phase with ethyl acetate makes it possible to isolate, after purification on a silica column, 2.15 g of (R)-diol (yield=48%, ee=92%).

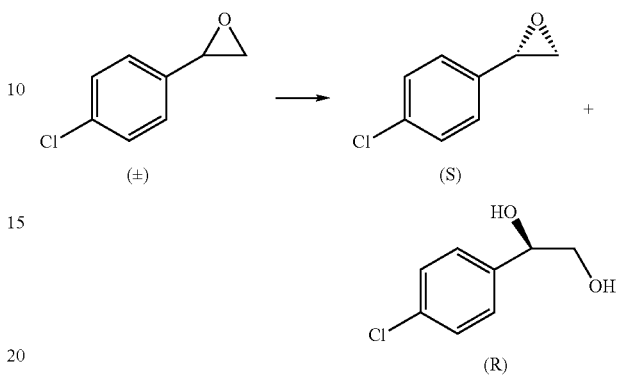

Example 4

4 g of para-nitrostyrene oxide (24 mmol or a concentration of 0.3 mol per litre of reaction medium) dissolved in 15 ml of DMSO is added to 60 ml of phosphate buffer (pH 7, 0.1 M). The temperature is adjusted to 27° C. and 0.7 g of purified (native) enzyme is added. After stirring for 32 hours the reaction medium is saturated with NaCl then extracted continuously with dichloromethane. Evaporation of the solvent followed by chromatography on silica makes it possible to isolate 1.8 g of (S)-epoxide (yield=45%, ee=96%) and 2.3 g of (R)-diol (yield=52%, ee=86%).

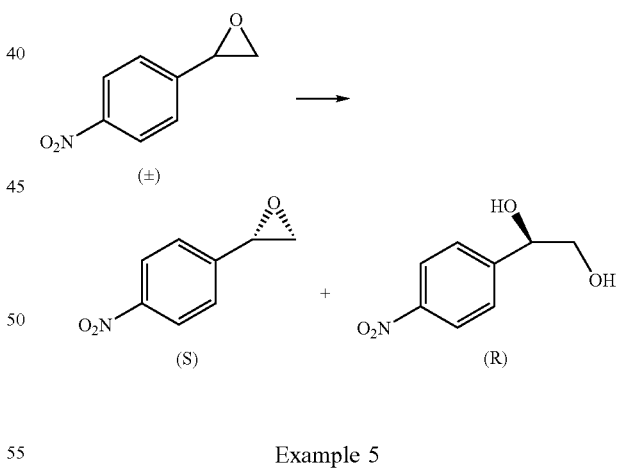

Example 5

1.5 g of para-isobutyl-α-methylstyrene oxide (7.9 mmol or a concentration of 0.25 mol per litre of reaction medium) is added to 30 ml of Tris buffer (pH 8, 0.4 M). The temperature is adjusted to 4° C. and 2.6 g of purified (native) enzyme is added. After stirring for 24 days at 4° C. the residual epoxide is extracted with pentane. Evaporation of the solvent makes it possible to obtain the unpurified (S)-epoxide (ee=96%). Extraction of the aqueous phase with ether makes it possible to isolate, after purification on a silica column, 0.91 g of (R)-diol (yield=55%, ee=70%).

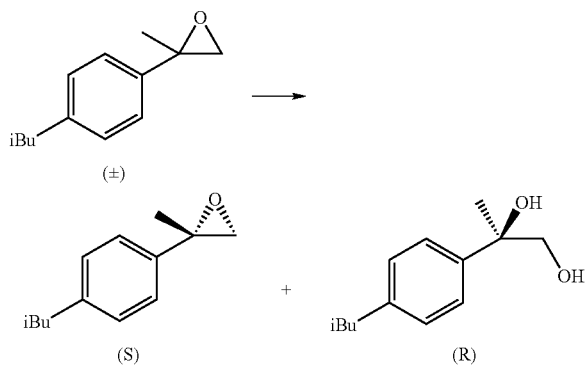

Example 6

1 g of phenyl glycidyl ether (6.7 mmol or a concentration of 3.3 mol per litre of reaction medium) is added to 1 ml of phosphate buffer (pH 7, 0.1 M). The temperature is adjusted to 27° C. and 25 mg of purified recombinant enzyme is added. After stirring for 15 hours at 27° C. all of the epoxide is converted to the corresponding racemic diol. Extraction with ethyl acetate makes it possible to isolate this diol at a quantitative yield.

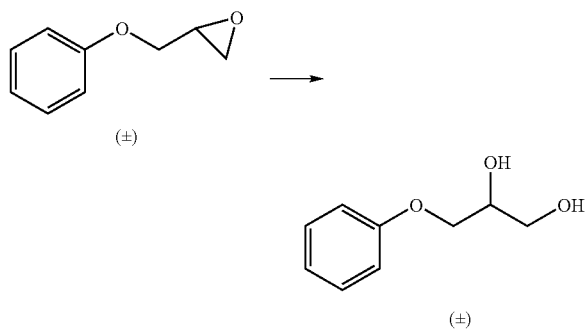

BIBLIOGRAPHY

Audier H. E., Dupin J. F., Jullien J. (1968) *Bull. Chem. Soc.,* 9, 3844–3847.
Arand M., Wagner H., Oesch F. (1996) *J. Biol. Chem.,* 271, 4223–4229
Arand M., Müller F., Mecky A., Hinz W., Urban P., Pompon D., Kellner R., Oesch F. (1999) *Biochem. J.,* 337, 37–43.
Archelas A., Furstoss R. (1997) *Ann. Rev. Microbiol.,* 51, 491–525
Archelas A., Furstoss R. (1998) *Trends in Biotechnology,* 16, 108–116
Beetham J. K., Grant D., Arand M., Garbarino J., Kiyosue T., Pinot F., Oesch F., Belknap W. R., shinozaki K., Hammock B. D. (1995) *DNA Cell Biol.,* 14, 67–71
Blée E., Schuber F. (1992) *Biochem. J.,* 282, 711–714
Borhan B., Jones A. D., Pinot F., Grant D. F., Kurth M. J., Hammock B. D. (1995) *Anal. Biochem.,* 231, 188–200
Chomczynski P., Sacchi N. (1986) *Anal. Biochem.,* 162, 156–159
Dansette P. M., Makedonska V. B., Jerina D. M. (1978) *Arch. Biochem. Biophys.* 187, 290–298
Delaage M. (1968) *Biochim. Biophys. Acta,* 168, 443–445
Friedberg T., Kissel W., Arand M., Oesch F. (1991) In *Methods in Enzymology* (Waterman M. R. and Johnson E. F., eds) Vol. 206, pp. 193–201, Academic Press, New York
Hammock B. D., Grant D. F., Storms D. H. (1997) In *Comprehensive Toxicology* (Sipes, I., McQueen C. and Gandolfi, A., Eds), pp 283–305, Pergamon Press, Oxford
Laemmli U. K. (1970) *Nature,* 227, 680–685
Lowry O. H., Rosebrough N. J., Farr A. L., Randall R. J. (1951) *J. Biol. Chem.,* 193, 265–275
Misawa E., Chan Kwo Chion C. K. C., Archer I. W., Woodland M. P., Zhou N.Y., Carter S., Widdowson D. A., Leak D. A., Leak D. A. (1998) *Eur. J. Biochem.,* 253, 173–183
Nellaiah H., Morisseau C., Archelas A., Furstoss R., Baratti J. C. (1996) *Biotech. Bioeng.,* 49, 70–77
Pedragosa-Moreau S., Archelas A., Furstoss R. (1993) *J. Org. Chem,* 58, 5533–5536
Pedragosa-Moreau S., Archelas A., Furstoss R. (1995) *Bull. Soc. Chem. Fr.* 132, 769–800
Pedragosa-Moreau S., Archelas A., Furstoss R. (1996) *J. Org. Chem.* 61, 7402–7407
Pedragosa-Moreau S., Morisseau C., Zylber J., Baratti J. C., Archelas A., Furstoss R. *Tetrahedron*(1997) 53, 9707–9714
Rink R., Fennema M., Smids M., Dehmel U., Janssen D. B. (1997) *J. Biol. Chem.,* 272, 14650–14657
Schurig V., Betschinger F. (1992) *Chem. Rev.* 873–888
Tomic M., Sunjeravic I., Savtchenko E. S., Blumenberg M. (1990) *Nucleic Acids Res.,* 18, 1656
Touhara K., Prestwitch G. D. (1993) *J. Biol Chem.,* 268, 19604–19609
Westkaemper R. B., Hanzlik R. P. (1980) *Anal. Biochem.,* 102, 63–67
Westkaemper R. B., Hanzlik R. P. (1981) *Arch. Biochem. Biophys.,* 208, 195–204
Wixtrom R. N., Hammock B. D. (1985) In *Biochemical Pharmacology and Toxicology* (Zakim D. and Vessey D. A., Eds) pp. 1–93, John Willey & Sons, New York.

What is claimed is:

1. A protein of the sequence SEQ ID NO: 2 purified to electrophoretic homogeneity from cultures of cells of strains of *Aspergillus niger*.

2. A recombinant protein of sequence SEQ ID NO: 2 corresponding to a recombinant fungal epoxide hydrolase obtained by transformation of suitable host cells by means of vectors containing the nucleotide sequence SEQ ID NO: 1 encoding the epoxide hydrolase of SEQ ID NO: 2.

3. A nucleotide sequence of SEQ ID NO: 1 encoding the epoxide hydrolase of SEQ ID NO: 2, the aforementioned sequence being of single-stranded or double-stranded form.

4. A vector containing a nucleotide sequence according to claim 3.

5. A host cell selected from the group consisting of bacteria, viruses, yeasts, fungi, plants and mammalian cells, the said host cell being transformed by a vector of claim 4, so that its genome contains a nucleotide sequence of SEQ ID NO: 1 encoding the epoxide hydrolase of SEQ ID NO: 2, the aforementioned sequence being of single-stranded or double-stranded form.

6. A method of preparation of epoxides and/or of enantiomerically pure vicinal diols comprising a stage of treatment of a mixture of diastereoisomeric epoxides, or of a chiral epoxide in racemic form, or of a prochiral epoxide, with a protein of sequence SEQ ID NO: 2 purified to electrophoretic homogeneity, or with a recombinant protein of sequence SEQ ID NO: 2, or with a host cell of claim 5 expressing a recombinant protein of sequence SEQ ID NO: 2.

7. A method of preparation of a recombinant protein of sequence SEQ ID NO: 2, comprising transforming host cells with a vector containing the nucleotide sequence of SEQ ID NO: 1, and purifying the recombinant protein of sequence SEQ ID NO: 2 produced by the said cells.

8. A method of preparation of protein of sequence SEQ ID NO: 2 purified to electrphoretic homogeneity from cultures of cells of strains of *Aspergillus niger*, comprising:

extracting the enzyme from cellular cultures of *Aspergillus niger*, by crushing the fungus using a press, followed by a stage of low-speed centrifugation, recovery of the supernatant, and, optionally, concentration of the same, and purifying the enzyme from the extract obtained in the preceding stage by successive passages through columns of DEAE-Sepharose, Phenyl-Sepharose, Mono Q and Superose 12.

* * * * *